United States Patent [19]
Toso

[11] Patent Number: 5,643,184
[45] Date of Patent: Jul. 1, 1997

[54] BACK SUPPORT WITH KNEE AND FOOT ENGAGING STRAPS

[76] Inventor: Victor Toso, 2438 Como Ave., SE., St. Paul, Minn. 55108

[21] Appl. No.: 543,643

[22] Filed: Oct. 16, 1995

Related U.S. Application Data

[63] Continuation of Ser. No. 106,567, Aug. 16, 1993, abandoned.

[51] Int. Cl.⁶ .............................. A47C 20/00; A61F 5/00
[52] U.S. Cl. ................... 602/19; 2/44; 450/155
[58] Field of Search ........................ 2/22, 46, 44, 45, 2/92, 69, 69.5; 450/156; 602/19, 32, 33; 606/241; 601/45; 128/874, 875, 876

[56] References Cited

U.S. PATENT DOCUMENTS

| 6,385 | 4/1849 | Pollard et al. | 601/45 |
| 68,521 | 9/1867 | Manley | 601/45 |
| 504,598 | 9/1893 | Leyda | 601/45 |
| 846,562 | 3/1907 | Grayson | 2/44 |
| 1,678,584 | 7/1928 | Branson | 2/44 |
| 4,819,846 | 4/1989 | Hannemann | 2/312 X |
| 5,001,791 | 3/1991 | Toso | 602/19 X |
| 5,201,448 | 4/1993 | Schue | 2/300 X |
| 5,256,119 | 10/1993 | Tudor | 128/882 |
| 5,334,134 | 8/1994 | Saunders | 602/19 |

OTHER PUBLICATIONS

Gershman, Maurice, "Self Adhering Nylon Tapes." The J.A.M.A., vol. 168, No. 7, Oct. 1958.

*Primary Examiner*—Jeanette E. Chapman
*Attorney, Agent, or Firm*—Aquilino & Welsh

[57] ABSTRACT

A back support for engaging the lower back region of a user, including a pair of inelastic straps and/or a combination of inelastic and elastic straps structured to engage the knees and the feet of a user. When the user is in a seated position and requires additional back support, the straps are connected to the feet and knees to exert a force on the back support for supporting the user's lower back.

20 Claims, 2 Drawing Sheets

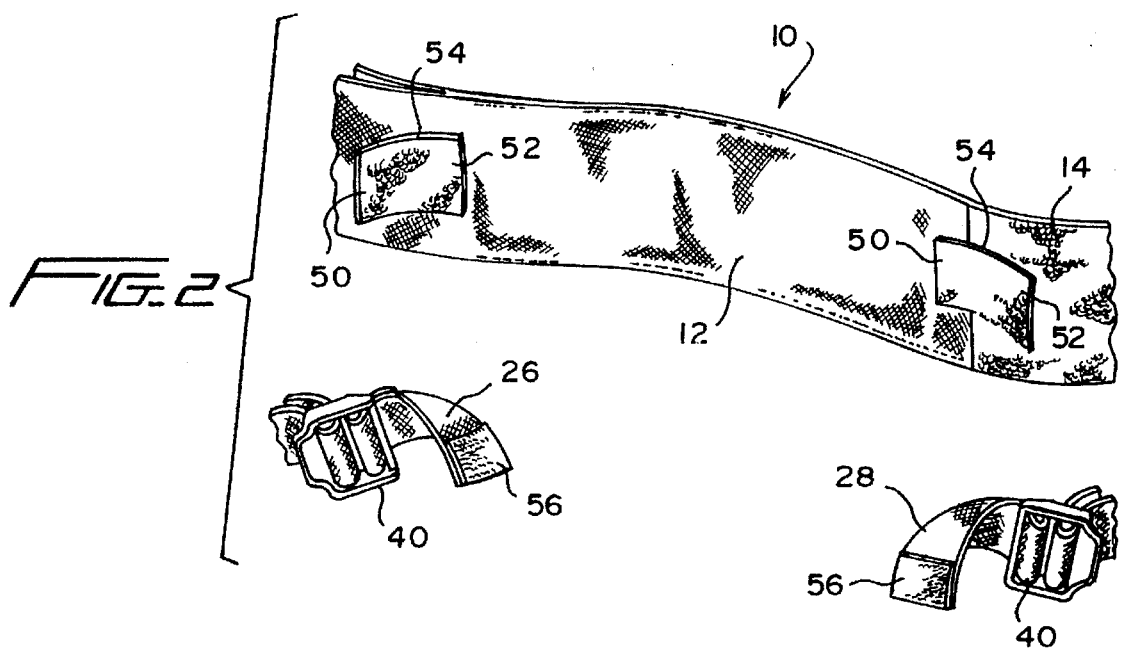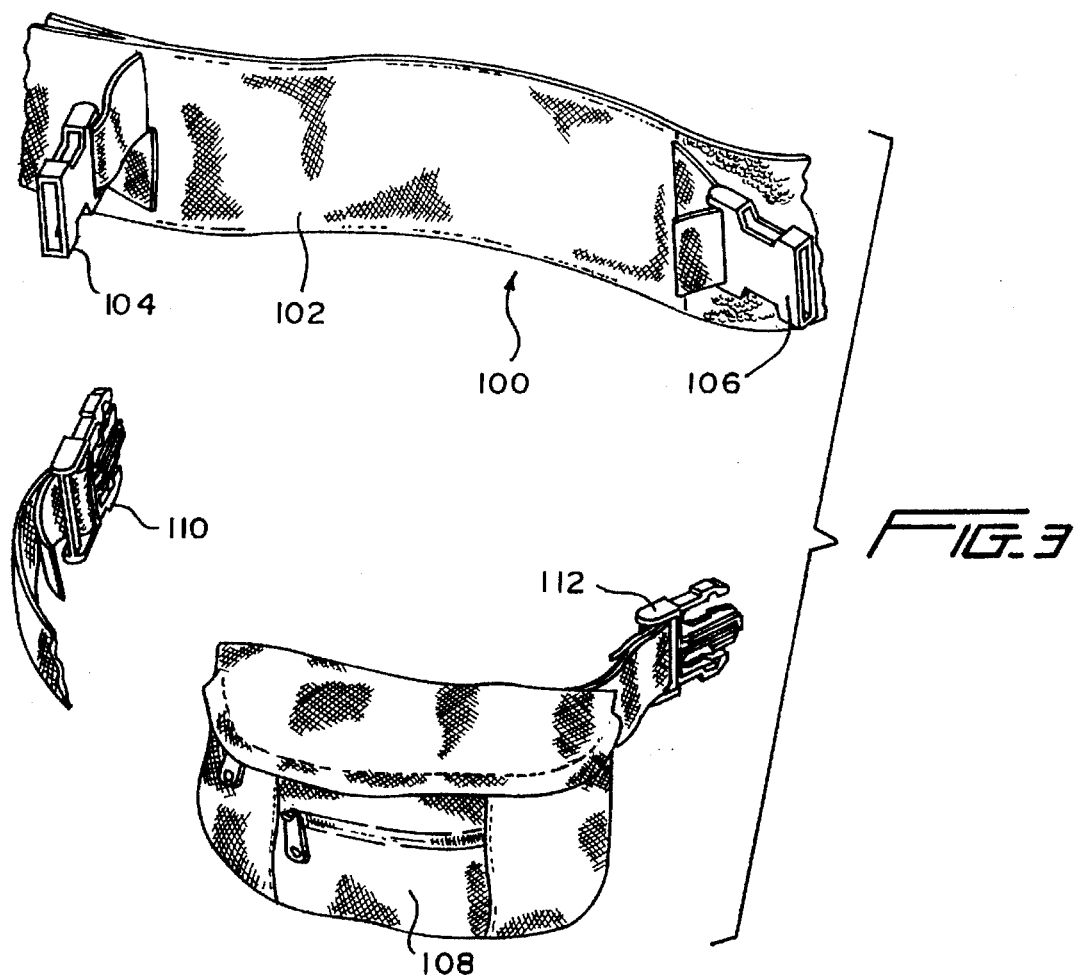

5,643,184

BACK SUPPORT WITH KNEE AND FOOT ENGAGING STRAPS

This is a continuation of application Ser. No. 08/106,567 filed on Aug. 16, 1993, now abandoned.

BACKGROUND OF THE INVENTION

The present invention relates to a back support, and in particular, to a back support for supporting the lower back of a person in a seated position.

In my prior U.S. Patents, I had developed a back support for eliminating discomfort when an individual is seated in an upright position on a flat surface and without a rigid back support, such as on the ground, a floor, or on a backless chair. These positions cause discomfort because of lack of support at the lumbar region, and they are particularly exaggerated with people who have poor posture and/or a weak back structure. As indicated in these patents, long periods of sitting in an upright position occur during various sporting activities and personal disciplines, such as meditation and yoga.

In my U.S. Pat. No. 4,773,106, a back support is disclosed, including a flexible, rectangular back supporting member which spans the lumbar region and a pair of elongated straps which engage the knees of the user when in the sitting position, whereby the force on the user's knees on the straps pulls the back supporting member against the lower back, enabling the user to sit upright comfortably for extended periods of time.

In my U.S. Pat. No. 4,813,080, a back support is formed integrally with an upper torso garment and includes a pair of straps to engage the knees of the user when the wearer is in a seated position so that the force of the wearer's knees on the straps pulls the back supporting member of the garment against the lumbar portion of the user to enable the wearer to sit upright comfortably for extended periods of time.

Still another U.S. Pat. No. , 5,001,791, shows a back support having an integral carrying case and a strap loop connector. In this back support structure, a closure means is integrally formed around the peripheral of the rectangular back supporting member, enabling the member to be folded upon itself and secured by the closure means, forming a case for carrying the elongated straps therein.

Other patents of interest are Japanese Serial No. 63-251009, U.S. Patent to Wildermouth (U.S. Pat. No. 2,280,274), Ziegler (U.S. Pat. No. 1,266,374) and Stevens (U.S. Pat. No. 3,295,517), and in addition, the patents cited against my three aforementioned patents described hereinabove.

SUMMARY OF THE INVENTION

The present invention relates to a lumbar back support for supporting a user in a seated position when a backrest is not available or to augment the support of a chair, automobile seat or other sitting device. The back support includes a generally rectangular member sized to fit the lower lumbar area of a person. The support includes a pair of elongated inelastic and/or elastic straps which are attached to opposite ends of the support member having foot engaging loops and knee engaging loops, which maintain pressure against the back support member and also maintain and locate the straps on the legs of the user, while at the same time providing freedom of movement for the legs of the user while the straps are being worn. With the back support in position, the user may apply pressure with a combination of both the feet and the knees, enabling the support to be pulled tightly against the user's lower back to provide support thereby.

The support further includes a belt member which may extend from the back support forwardly around the waist of the user, enabling the back support to be held in position should the straps become disengaged from the knees and feet of the user. In addition, the straps can be detached to allow the elastic waistband to serve separately as a lifting support by cinching it up when the user is going to lift something heavy. The back support can also serve as a support belt by wearing it around the waist and cinched up to support the user when walking.

The present invention also contemplates an integral carrying case which may be integrally formed with or buckled directly to the back support when the straps are removed, so that the straps may be carried in the case for storage and/or when the support is worn when the user is walking.

A primary use of the present invention is to support a user's back when driving an automobile. The use of elastic materials for the knee loops in combination with inelastic straps provides enough "give" to provide a comfortable fit around the user's knees without having the straps disengage from the knees. Because of the elasticity of the knee loops, the pressure from the feet extends to the lower back while keeping the legs free to move and to be rapidly extended, as may be required when driving.

Still another feature of the present invention is the ability of the foot engaging loops to be removed from the straps at the adjustment buckle to permit laundering, since this part will be subject to soiling.

Among the objects of the present invention is to provide a back support device using both the feet and the knees to exert pressure on the back support member to support the back of the user.

Another object of the present invention is to provide a back support which is adjustable and which can be worn when the straps are not in use.

These and other objects and advantages of the present invention will become apparent from the following detailed specification when viewed in conjunction with the accompanying drawings.

BRIEF DESCRIPTION OF THE DRAWINGS

FIG. 2 is a rear partial view of FIG. 1.

FIG. 3 is a rear elevational view of an alternate embodiment of the present invention.

DESCRIPTION OF THE PREFERRED EMBODIMENTS

Figure 1:
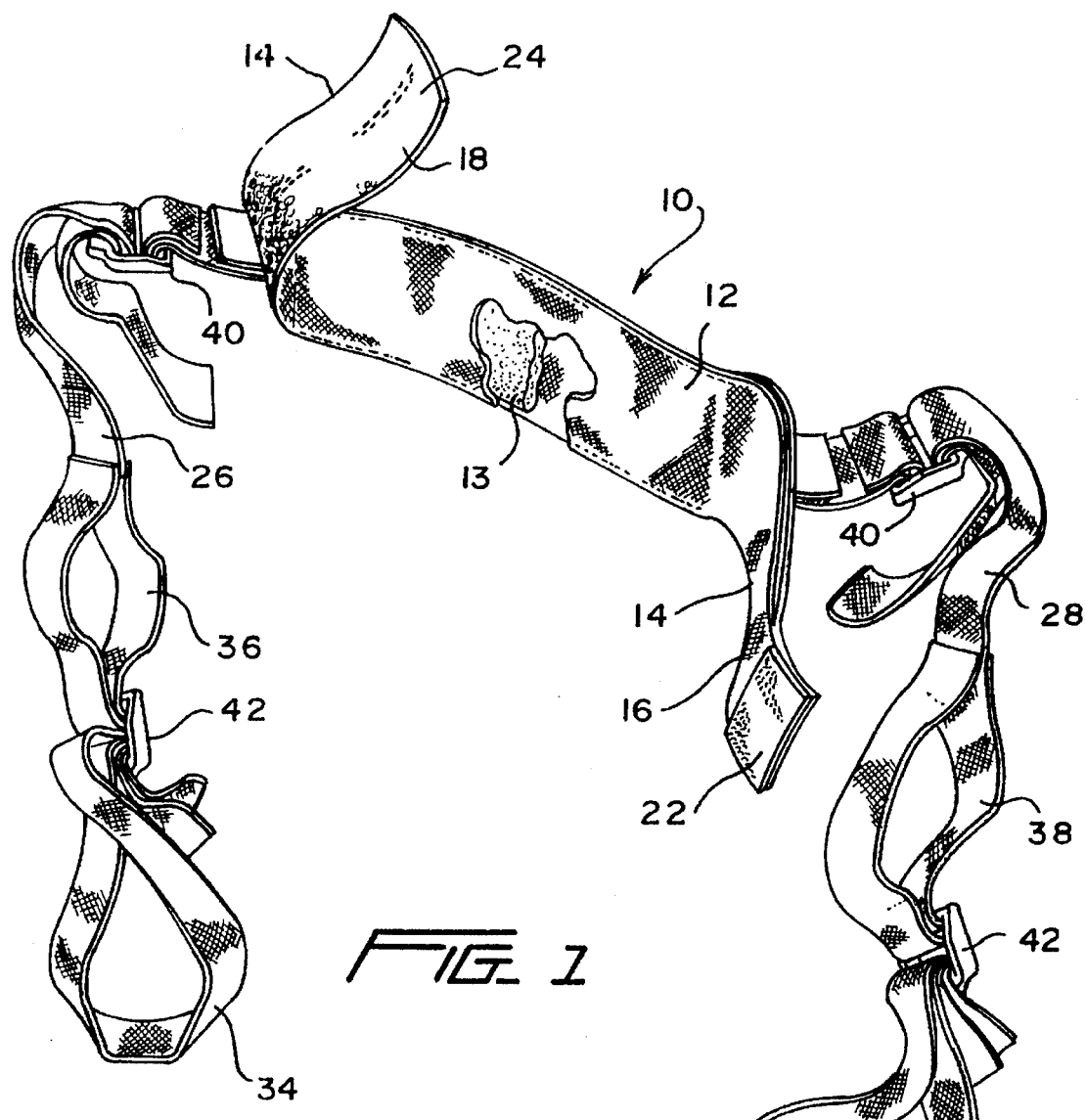
FIG. 1 is a perspective view of the back support in accordance with the present invention.
Figure 4:
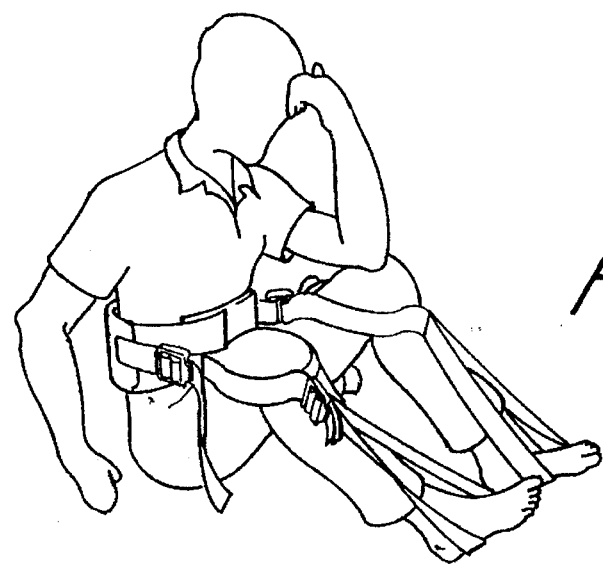
FIG. 4 is a view of an individual seated on a ground surface wearing the back support of the present invention.

The back support of the present invention is adapted to engage the lumbar region of a wearer and includes a pair of straps which extend longitudinally from the ends of the support member and which include both knee engaging and foot engaging loops for the feet and knees of the user which maintain the back support in position on the user and also which exert a force against the lower back portion of the user providing support.

Referring to the drawings, back support 10 of the present invention includes a back support panel 12 having an elongated and generally rectangular shape. The panel may include a cushion or pad 13 and/or reinforced to provide support and comfort for a user. Preferably, the panel is sized to substantially span the width of a lower back of a user and also to span the height of the lumbar portion of the user. Preferably, the support panel may be made in a unitary size in order to fit the majority of individual users, however, it will be appreciated that the panel may be made larger or smaller to accommodate different sized people. The panel includes an integrally formed attachment member which allows the panel to be adjustably positioned on the user. In the embodiment shown, the attachment is formed of a belt 14 made of two sections 16 and 18 which are fixed through opposite ends of the panel 12. The belt 14 includes a hook and loop type separable fastener. A hook-type separable fastener member 22 is attached to the free end of the belt section 16 and a loop type separable pad member 24 formed along the entire length of the belt section 18. Preferably, at least one of the belt sections is elasticized to further aid in the adjustability of the closure. It will be appreciated that with the panel 12 in place against the lumbar portion of the back of the user, the belt sections 16 and 18 are brought forward around the waist of the user and attached together in a comfortable position with the separable fastener closure.

A pair of straps 26 and 28 are also attached to opposite ends of the back support panel 12. The straps 26 and 28 are formed in a length to engage the feet of the user by means of loop members 34 and 36 at the free end of each strap 26 and 28. The straps 26 and 28 also include intermediate knee engaging loops 36 and 38 formed approximately mid-way between the fixed and free ends of the strap members. Each strap includes a pair of adjusting buckles 40 and 42 which enable the overall length of the straps 26 and 28 to be adjusted for the size of a particular user. Buckle 40 adjusts the distance between the knee engaging loops 36 and 38 and the support panel 12. Buckle 42 adjusts the length of the foot loops 34 and 36. Another hook and loop type separable fastener 50 is formed at each end of the back support panel 12 and connects the straps 26 and 28 directly to the back support panel 12. This enables the straps 26 and 28 to be removed when they are not in use, permitting the user to wear the back support panel simply as a brace. The separable fastener 50 includes a loop engaging member 52 attached to a flap 54 on the panel 12 and a hook engaging member 56 attached to each end of the straps 26 and 28. It will be appreciated that other fasteners may be used to connect the straps 26 and 28 to the panel as described hereinbelow.

In use, the back support panel 12 is placed adjacent the lumbar region of a user and the belt 14 is tightened around the waist using the hook and loop separable fasteners 22 and 24. With the user in a seated position, foot loops 34 and 36 are placed across the soles of the feet at the instep and the knee loops 36 and 38 are engaged by the knees of the user. It will be appreciated that the length of the straps may be adjusted to conform to the particular anatomical features of any given user using the buckles 40 and 42.

FIG. 3 shows an alternate embodiment of a back support 100 having a back support panel 102 which uses a pair of quick release female buckles 104 and 106 in place of the hook and loop separable fasteners of the first embodiment. The buckles 104 and 106 attach straps (not shown) having the knee and foot loops to the back support panel 102 using male buckles (not shown). This arrangement permits attachment of a pack 108 which may be attached to the back support panel 102 using quick release male buckles 110 and 112 for storage of straps (not shown) when they are not in use. Alternately, the carrying case may be formed integral with the back support panel.

Other modifications or alterations to the above described invention may be made. For example, the back support may be attached to the torso of the user by means of a belt buckle or other fastener rather than the hook and loop type separable fastener shown. The back support may be also made of rigid or semi-rigid sections and specific individuals could be fitted with supports that are molded exactly to their body contours. As indicated above, the size of the back support section and the straps may be adjusted for various users in keeping within the scope and spirit of the present invention as defined in the following claims.

I claim:

1. A back support device and integrally formed attachment member for supporting the lower back region of a user in a seated position comprising:

a back support panel spanning the lower back region of a user, the back support panel is sized to substantially span the width of a lower back of a user and also to span the height of the lumbar portion of the user, accordingly, the back support panel includes support elements designed to provide support and comfort to the user;

a pair of elongated straps having thick ends attached to and extending from opposite ends of said back support panel; said straps including a means for engaging the knees of the user formed proximate a mid portion of said elongated straps and said straps including means for engaging the feet of the user at the free ends of said elongated straps; said integrally formed attachment member including an adjustable belt extending from said opposite sides of said back support panel proximate said fixed ends of said elongated straps and said opposite ends of said back support panel, wherein said belt is distinct from the back support panel and said pair of straps;

said belt including an adjustable closure to be fastened around the waist of the user to maintain the back supporting member in place against the lower back region of the user; and, whereby the force of said user's legs on the straps pulls said back supporting panel against the lower back of said user, enabling said user to sit upright comfortably for extended periods of time.

2. The back support device of claim 1 wherein said means for engaging the knees of the user are knee loops and said means for engaging the feet of the user are foot loops.

3. The back support device of claim 1 wherein said back support panel is formed of flexible material; said panel being formed with a length substantially spanning the width of the lower back of the user and a height spanning the user's lumbar region.

4. The back support device of claim 1 further including a cushion integrally formed therewith.

5. The back support device of claim 1 wherein said closure member on said belt is adjustable to accommodate a variety of differently sized users.

6. The back support device of claim 5 wherein said adjustable closure is a separable fastener having a first separable fastener member connected to a portion of the belt connected to a first end of said back support member and a second separable fastener member connected to a second portion of the belt connected to a second opposite end of said back support.

7. The back support device of claim 6 wherein said separable fastener member includes a hook-type separable fastener element and a loop-type separable fastener element.

8. The back support device of claim 1 further including means for adjusting the length of said elongated straps.

9. The back support device of claim 1 further including means for connecting said straps to said back supporting panel.

10. The back support device of claim 9 wherein said connecting means is formed of separable fastener members having a first separable fastener connected to a tab on said back support panel, and a second separable fastener member connected to an end of each elongated strap.

11. The back support device of claim 9 wherein said attaching means for attaching said straps to said back support panel is a quick release buckle.

12. The back support device of claim 2 including a second adjusting member on each of said elongated straps for adjusting the length of said foot loops.

13. The back support device of claim 12 wherein said foot loops are removably attached to said second adjusting member.

14. The back support device of claim 1 further including a carrying case attachable to said back support panel for carrying said straps when not in use.

15. The back support device of claim 1 including an elasticized portion of said elongated straps made of elasticized material.

16. The back support device of claim 15 wherein said elasticized portion includes loops to engage the knees of the user.

17. The back support device of claim 2 wherein said knee loops are elasticized.

18. A method of supporting the lumbar region of the back of a user in a seated position, comprising the steps of:

locating a support member on the lumbar region, the support member being sized to substantially span the width of a lower back of a user and also to span the height of the lumbar region of the user, accordingly, the support member includes support elements designed to provide support and comfort to the user;

attaching a first strap and a second strap to said support member adjacent the side of the user, said first strap and said second strap each including a first section and a second section;

engaging the knees of a user with said first section of said first strap and said first section of said second strap;

engaging the feet of a user with said second section of said first strap and said second section said second strap; and, securing a back support around the waist of the user independent of said first strap and said second strap as well as the support member, with a belt member having an adjustable closure and exerting a force with the knees and feet against the straps, pulling said support member against the lumbar region for supporting the same.

19. The method of claim 18 including the steps of forming loops in said first strap and said second strap to engage the knees and to engage the feet of the user.

20. The device of claim 1 wherein said belt has a width corresponding to the width of said back support panel to which it is attached.

* * * * *